United States Patent [19]

Lazarus

[11] Patent Number: 4,787,899
[45] Date of Patent: Nov. 29, 1988

[54] INTRALUMINAL GRAFT DEVICE, SYSTEM AND METHOD

[76] Inventor: Harrison M. Lazarus, 324 Tenth Ave.-260, Salt Lake City, Utah 84103

[21] Appl. No.: 940,907

[22] Filed: Dec. 10, 1986

Related U.S. Application Data

[63] Continuation of Ser. No. 559,935, Dec. 9, 1983, abandoned.

[51] Int. Cl.$^4$ .......................... A61F 2/06; A61B 17/04
[52] U.S. Cl. .................................... 623/1; 128/331 R
[58] Field of Search ........... 128/303 R, 334 R, 334 C; 623/1

[56] References Cited

U.S. PATENT DOCUMENTS

| | | | |
|---|---|---|---|
| 3,334,629 | 11/1964 | Cohn | 128/325 |
| 3,494,006 | 2/1970 | Brumlik | |
| 3,540,431 | 11/1970 | Mobin-Uddin | 128/1 R |
| 3,562,820 | 2/1971 | Braun | 128/334 R |
| 3,834,394 | 9/1974 | Hunter et al. | 128/325 |
| 3,874,388 | 4/1975 | King et al. | 128/334 R |
| 3,908,662 | 9/1975 | Razgulov et al. | 128/334 R |
| 3,938,499 | 2/1976 | Bucalo | 128/334 C |
| 3,938,528 | 2/1976 | Bucalo | 128/334 C |
| 4,006,747 | 2/1977 | Kronethal | 128/335 |
| 4,047,252 | 9/1977 | Liebig et al. | 623/1 |
| 4,056,854 | 11/1977 | Boretos et al. | 128/1 R |
| 4,140,126 | 2/1979 | Choudhury | 128/325 |
| 4,198,982 | 4/1980 | Fordner et al. | 128/334 C |

OTHER PUBLICATIONS

Krause et al., "Early Experience with the Interluminal Graft Prosthesis", Amer. Jour. of Surgery, 145:619-622, May 1983.
Dotter et al., "Transluminal Expandible Nitinol", Radiology, 147:259-260, Apr. 1983.
Balko et al., "Transfemoral Placement of Intraluminal Polyurethane Prosthesis for Abd. Aortic Aneurysm", Jour. Surg. Res., 40:305-309 (1986).
Andrew Cragg et al., "Nonsurgical Placement of Arterial Endoprostheses: A New Technique Using Nitinol Wire", Radiology, 147:261-263, Apr. 1983.
D. Maass, "Radiological Follow-Up of Transluminally Inserted Vascular Endoprosthesis, An Experimental Study Using Expanding Spirals", Radiology, 152:659-663 (1984).
Kaj Johansen, "Aneurysms", Scientific American, 247:110-125, Jul. 1982.
Advertising flyer for Greenfield Vena Cava Filter a Product of Medi-Tech, Inc. of Watertown, Massachusetts Illustrates a Stainless Steel Device for Interluminal Placement Configured to Prevent Pulmonary Embolism. .

Primary Examiner—Richard J. Apley
Assistant Examiner—David J. Isabella
Attorney, Agent, or Firm—Trask, Britt & Rossa

[57] ABSTRACT

An intraluminal grafting system includes a hollow graft which has a plurality of staples adapted proximate its proximal end. The system includes a guide for positioning the proximal end of the graft upstream in a lumen which may be a blood vessel or artery. The back of the guide has a cavity into which the proximal end of the graft is retained. A rod extends from the cavity to exterior the lumen for manipulation by the user. A tube is positioned over the rod to extend from the cavity and through the graft to exterior the lumen. The tube has an inflatable membrane proximate the cavity end thereof which is in communication via a channel with inflation and deflation means located exterior the lumen. With the inflatable membrane deflated, the guide means is positioned into the lumen and manipulated to a desired location. The inflatable membrane is inflated to place a force against the staples as the guide is manipulated by the rod away from the graft. The force exerted by the inflatable membrane forces the staples into the lumen.

7 Claims, 2 Drawing Sheets

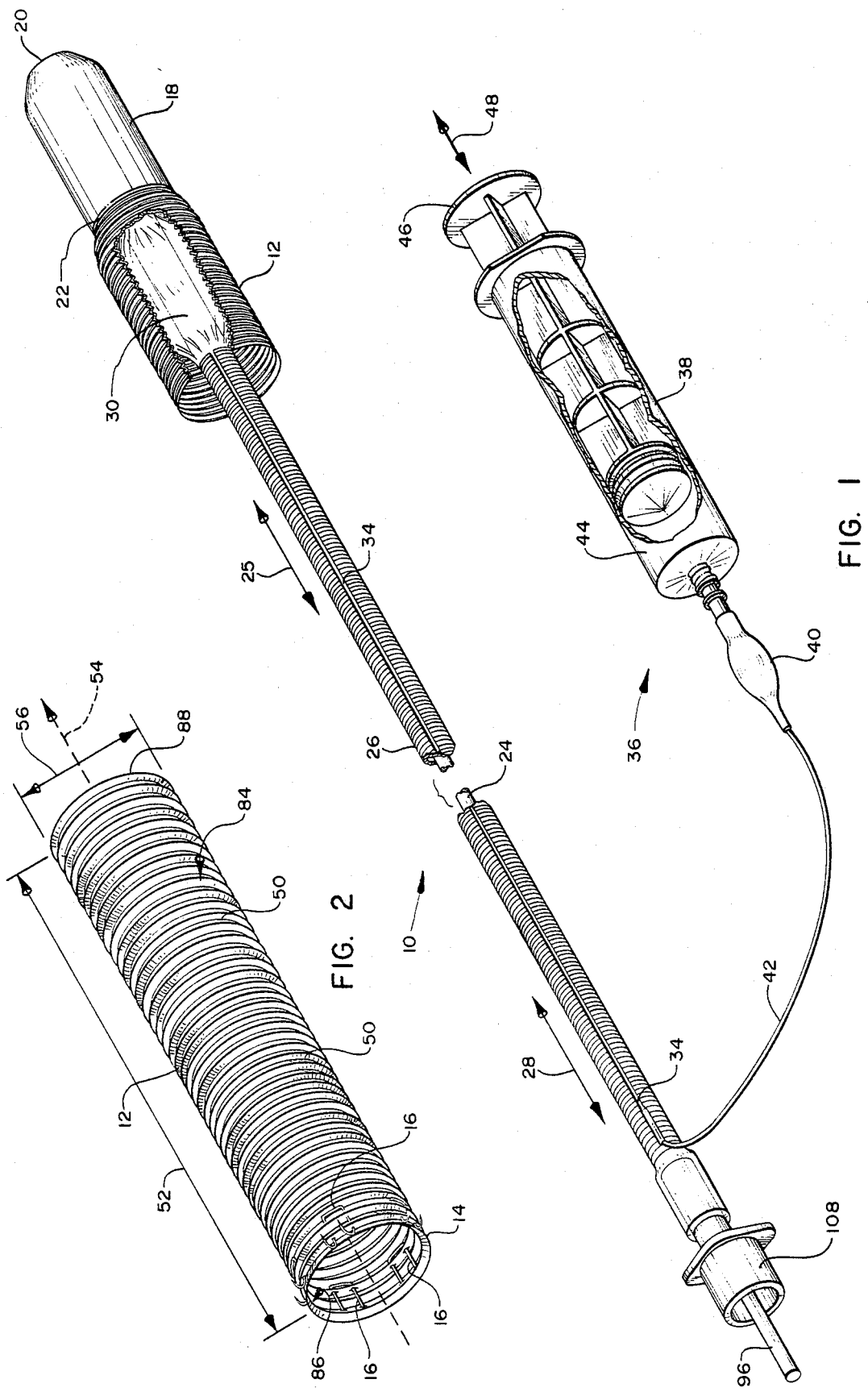

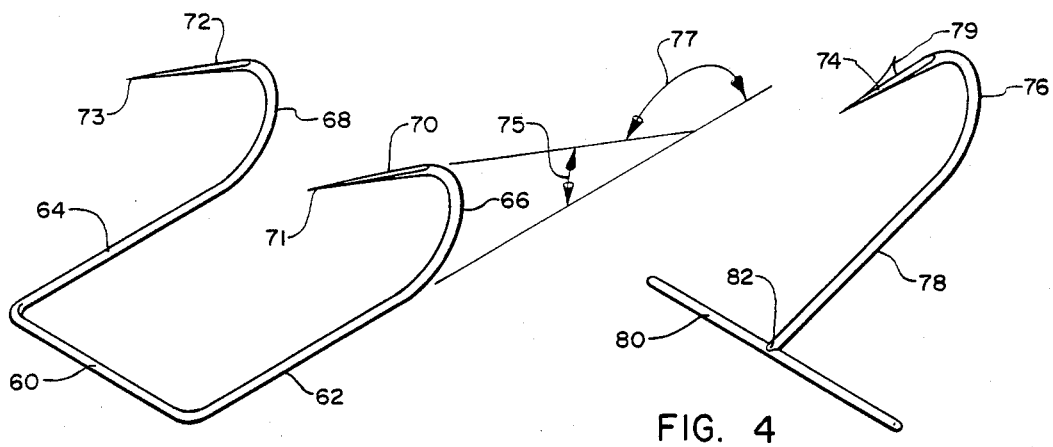
FIG. 3
FIG. 4
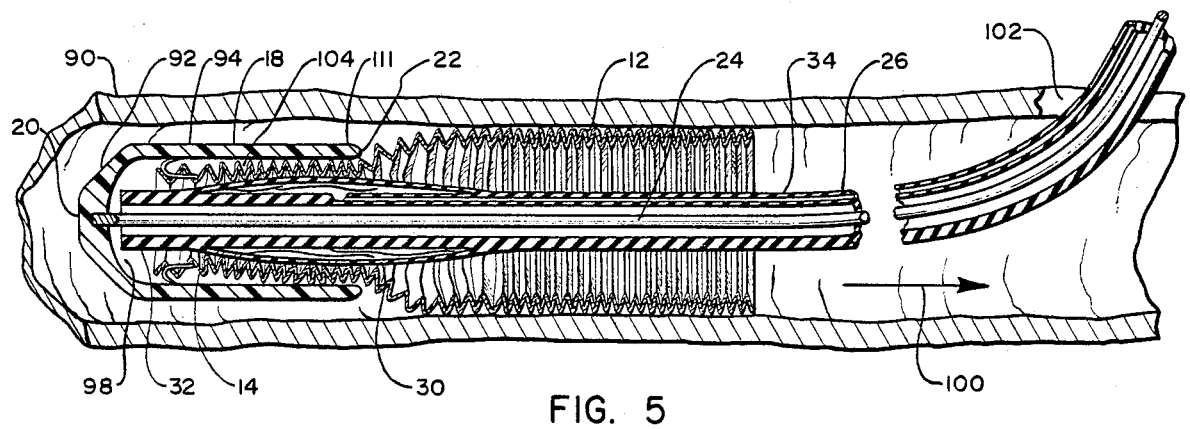
FIG. 5
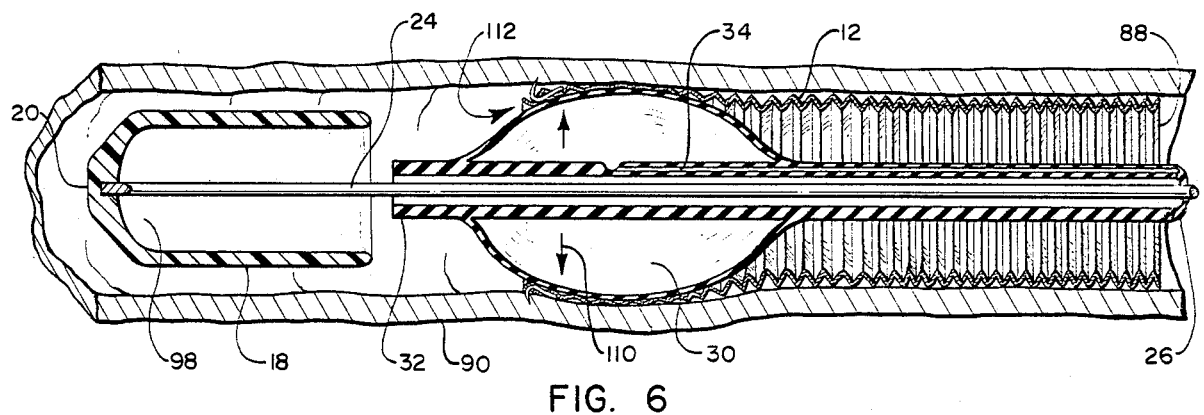
FIG. 6

INTRALUMINAL GRAFT DEVICE, SYSTEM AND METHOD

This is a continuation of application Ser. No. 559,935 filed Dec. 9, 1983 now abandoned.

BACKGROUND OF THE INVENTION

1. Field

This invention relates to medical prosthesis and more particularly to a graft prosthesis for placement within a corporeal lumen, such as a blood vessel or artery.

2. State of the Art

Various body lumens, such as blood vessels or arteries, suffer deterioration or other trauma such that repair is necessary. For example, various types of aneurysms or other deteriorative diseases may affect the ability of the lumen to conduct fluids and in turn may be life-threatening. In some cases the damaged lumen is repairable only with the use of an artificial lumen. For repair of vital lumens such as the aorta, such surgical repair is significantly life-threatening. Surgical techniques that have been employed involve major surgery in which an artificial lumen is inserted into the diseased or obstructed lumen. That is, the damaged or diseased portion of the lumen may be surgically removed or by-passed and an artificial lumen inserted and stitched to the ends of the lumen which were created by the removal of the diseased portion. Kaj Johansen, *Aneurysms*, Scientific American, 247: 110–125, July 1982. A variation of the typical suturing technique is described by Albert W. Krause, et al, *Early Experience With the Intraluminal Graft Prosthesis*, American Journal of Surgery, 145: 619–622, May 1983. The device illustrated in U.S. Pat. No. 3,908,662 to Razgulov et al is an example of a device to be used in such a surgical procedure.

Other devices for the repair of lumens such as blood vessels and arteries include a nitinol coil with a graft. The nitinol coil is reduced in dimension when cool. When placed in the body it heats up returning to a preselected dimension to hold a graft within a lumen. Such devices are discussed in detail in Charles T. Dotter, et al, *Transluminal Expandable Nitinol Coil Stent Grafting: Preliminary Report*, Radiology 147: 259–260, April 1983, and Andrew Cragg, et al, *Nonsurgical Placement of Arterial Endoprostheses: A New Technique Using Nitinol Wire*, Radiology 147: 261–263, April 1983. The use of devices such as the nitinol wire discussed above is regarded as not desirable because there is a danger of penetrating the lumen wall and damaging it during the emplacing process.

U.S. Pat. No. 4,140,126 to Choudhury discloses a device for intraluminal repair of an aneurysm. This device is positioned in a vessel in a collapsed form and then hooked into the vessel with hooks that are mechanically extended by the user. This device is mechanically complex and could be unreliable.

Other intraluminal devices are used but not for the repair of a diseased lumen. U.S. Pat. No. 3,874,388 to King et al discloses a system for closing off a septal defect or shunt in the intravascular system in the myocardial area. U.S. Pat. No. 3,334,629 to Cohn discloses a device for restricting the flow of blood. U.S. Pat. No. 4,056,854 to Boretus et al teaches construction and placement of an artificial aortic heart valve. U.S. Pat. No. 3,834,394 to Hunter et al teaches construction of an intraluminal device to occlude a blood vessel. U.S. Pat. No. 3,540,431 to Mobin-Uddin teaches construction of an umbrella-like filter for intraluminal use. MEDI-TECH, Inc. of Watertown, Mass. also sells a device known as the GREENFIELD ™ Vena Cava filter for intraluminal placement. U.S. Pat. No. 3,938,528 discloses a device that is implanted into the vas-deferens or similar lumen for the splicing of the lumen parts.

None of the devices noted above provide for a reliable and quick means or method to intraluminally repair a lumen.

SUMMARY OF THE INVENTION

An artificial intraluminal graft device for placement in a fluid conducting corporeal lumen has a hollow graft of preselected cross-section and length. The proximal end of the graft is placed upstream within the lumen. The graft is deformable to substantially conform to the interior surface of the lumen. A plurality of staples are adapted proximate the proximal end of the lumen and extend therethrough for stapling the graft to and within the lumen.

The staples have a lumen engaging member exterior the graft. The lumen engaging member is angulated in a downstream direction and has a distal end for engaging the lumen. The staples preferably have an axial member extending generally in an axial direction along the interior surface of the graft. In another embodiment, the staple has a first end extending through the graft and a retention member connected thereto for retaining the graft and the staple in relation to each other.

In another embodiment each staple has a base with two legs extending substantially normal thereto to be essentially U-shaped. The base is exterior the graft with the legs extending inwardly through the graft and axially along the interior surface thereof. Each leg has a transverse member connected thereto along its length extending outwardly through the graft. A lumen engaging member is connected to the distal end of each transverse member.

Preferably the graft is made of Teflon, nylon, dacron or the like. Prior to emplacement, the graft is formed to be substantially cylindrical in shape and formed to have a plurality of substantially evenly placed circumferential bifolds along the length thereof.

The system for intraluminally engrafting the hollow graft has placement means for emplacing the graft into said lumen and positioning it at a preselected position within the lumen and for causing at least one of said staples to engage the lumen. The placement means includes a guide shaped and sized for positioning within the lumen. The guide has a rod adapted to the back thereof which extends therefrom and through the hollow graft to exterior the lumen for manipulation by the user. The guide also has means to retain the proximal end of the graft for positioning the graft in the lumen. The placement means also includes operation means for removing the graft from the guide means and for positioning the staples into the lumen.

In a preferred embodiment of the system, the guide means back has a cavity formed therein with said rod centrally positioned therein. The proximal end of the graft is retained within the cavity. Preferably, the operation means includes a hollow tube for slideable positioning over the rod. The tube extends from the cavity through the graft to exterior the lumen. The tube has an inflatable membrane proximate the cavity end interconnected by a channel to an inflation deflation means exterior the lumen. Upon inflation, the guide can be urged forwardly with the membrane holding the graft in place and exerting a force to cause the staples to engage the lumen.

BRIEF DESCRIPTION OF THE DRAWINGS

In the drawings, which illustrate the best mode presently contemplated for carrying out the invention, FIG. 1 is a cut-away perspective view of an intraluminal graft system of the instant invention;

FIG. 2 is a perspective view of an intraluminal graft device of the instant invention;

FIG. 3 is an enlarged view of a staple for use with the intraluminal graft of the instant invention;

FIG. 4 is a perspective enlarged view of an alternate staple for use with the instant invention; and FIGS. 5 and 6 are cross-section views of the intraluminal graft device and placement means of the instant invention showing an intraluminal graft being emplaced into a lumen.

DESCRIPTION OF THE ILLUSTRATED EMBODIMENT

FIG. 1 illustrates a system 10 for artificially and intraluminally engrafting in a fluid conducting corporeal lumen. The system includes a hollow graft 12 of preselected cross-section and length. The graft 12, as more fully shown in FIG. 2, has a proximal end 14 for placement upstream within the lumen. A plurality of staples 16 are adapted to the graft 12 proximate the proximal end 14. The staples extend through the graft for stapling the graft to and within the lumen.

The system 10 includes placement means for inserting the graft 12 into the lumen, for positioning the graft 12 at a preselected position within the lumen, and for causing at least one of the staples 16 to engage the lumen. The placement means includes a guide 18 which has a front 20 and a back 22. A rod 24 is adapted to the back 22 of the guide 18 and is sized in length 25 to extend exterior the lumen for manipulation by the user. The placement means includes operation means for removing the graft 12 from the guide 18 and for positioning the staples 16 into the lumen.

The guide 18 is sized for positioning in the lumen. As best seen in FIGS. 5 and 6, a cavity 98 is formed in the back 22 of the guide 18 to retain the proximal end 14 of the graft 12 for and during positioning of the graft 12 in the lumen.

The operation means preferably includes a hollow tube 26 for slideable positioning over the rod 24. The tube 26 is sized in length 28 to extend from the cavity 98 formed in the back 22 of the guide 18 to exterior the lumen. The tube 26 has an inflatable membrane 30 sized to fit within the graft 12 and positioned proximate the cavity end 32 (FIG. 4) of the tube 26. A channel 34 is associated with the tube 26 and is in communication from the inflatable membrane 30 along the length 28 of the tube 26 to the inflation means 36 exterior the lumen.

As seen in FIG. 1, the inflation means 36 is a syringe mechanism 38 connected through a connector 40 via an extension tube 42 to the channel 34. Those skilled in the art will recognize that the tube 26 with the channel 34 and an inflatable membrane 30 are very similar in function to a balloon dilation catheter. It will be also recognized that the syringe is a conventional syringe having a sleeve 44 within which a hand actuated piston 46 is sealably and slideably movable in an inwardly and outwardly direction 48 to insert a fluid via the tube 42 nd channel 34 to the membrane 30 to respectively inflate and deflate the membrane 30. The fluid inserted to inflate may be a saline solution or such other fluid as desired by the user. Of course the fluid may be extracted to deflate the membrane 30 by operating the piston 46 in an outward direction 48.

The artificial graft 12, shown in FIG. 2, is preferably made of a deformable material having a high tissue ingrowth rate. It is preferably formed to have a plurality of substantially evenly spaced circumferential bifolds 50 along the length 52 of the graft 12. The use of a material such as knitted dacron formed with bifolds 50 allows the graft 12 to readily deform both axially 54 and radially 56. Therefore, when emplaced, the graft 12 may readily conform to the interior shape of the lumen, as more fully discussed hereinafter. The length 52 of the graft 12 is selected by the user. Typically the length 52 will be selected to be longer than the diseased portion of the lumen to be repaired. The radial 56 or cross-sectional size is also selected by the user typically to substantially conform to or be slightly larger than the interior cross-section of the involved lumen.

As shown in FIG. 2, a plurality of staples 16 are positioned about the circumference of the substantially cylindrically shaped graft 12. The preferred staples are shown in FIG. 3 in an enlarged view. The preferred staples have a base 60 with two legs 62 and 64 extending substantially normal to the base 60 to be essentially U-shaped. Each leg 62 and 64 has respectively transverse members 66 and 68 which extend outwardly or away from the legs 62 and 64. Lumen engaging members 70 and 72 are connected to the transverse members 66 and 68, respectively. As shown in FIG. 3, the transverse members 66, 68 are preferably unitarily formed as an extension of the staple legs 62 and 64 to extend outwardly and essentially normal to the plane of the base 60 and legs 62, 64. The transverse members 66 and 68 bend in a direction toward the base 60 to become the lumen engaging members 70 and 72. Most preferably the staple is unitarily formed by bending wire brad material to the desired angular positions to form the base 60, legs 62, 64, transverse members 66, 68 and lumen engaging members 70 and 72. It should be noted that the transverse members 66 and 68 together with the lumen engaging members 70 and 72 are preferably hook-like with the tips 71 and 73 of the lumen engaging members 70 and 72 angulated downstream at an angle 75 in magnitude from about 75° to about 15°. Most preferably the members 70 and 72 are directed substantially directly downstream (i.e., 105°-180° bend 77). Further, the ends 71 and 73 are sharp to facilitate engagement with the lumen. Also, the ends 71 and 73 may be barbed 79 like a fish hook, if desired, as shown in FIG. 4. Of course, the staples are preferably made of a stainless steel or other material acceptable for use in the corporeal environment.

FIG. 4 shows an alternate staple in which the lumen engaging member 74 is illustrated to be connected to a transverse member 76 which extends away from an axial member 78. A retention member 80 is connected to the first end 82 of the axial member 78.

The staple of FIG. 3 is preferably positioned within the graft 12 (FIG. 2) so that the base 60 is on the exterior surface 84 of the graft 12. The legs 62 and 64 extend through the graft 12 and extend along the interior surface 86. The transverse members 66 and 68 extend through the graft in a generally outward or radial direction 56. The lumen engaging members 70 and 72 connected to the transverse members 66 and 68 angulate rearwardly or in a downstream direction towards the distal end 88 of the graft 12, it being remembered that the proximal end 14 is positioned in the upstream direction of the lumen.

It can be seen that other staples of similar construction such as that shown in FIG. 4 may be similarly inserted so that, for example, an axial member 78 extends generally in an axial direction 54 along the interior surface 86 of the graft 12, and so that the transverse member 76 extends generally outward and radially 56 through the graft 12 with the lumen engaging member 74 angulated downstream or toward the distal end 88. An optional barb 79 is shown as part of the member 74.

Referring now to FIG. 5, portions of the system 10 for artificial intraluminal engrafting are shown cross-sectionally within a lumen 90. The system 10 including the graft 12 and guide 18 may be constructed in a variety of different sizes in order to accommodate and be compatible with a variety of differently sized (in cross-section) corporeal lumens. In FIGS. 5 and 6, the guide 18 is shown to be smaller than the lumen 90 so that the various surfaces may be better illustrated. Typically, the cross-sectional size (i.e., area normal to axis 54) of the pertinent system components such as the guide 18 and graft 12 are selected to be substantially the same as or slightly larger than the lumen 90. It should be further recognized that the corporeal lumen illustrated is substantially circular in cross-section. However, lumens such as blood vessels or arteries may vary widely in cross-section along their length but will elastically deform to receive the guide 18 and other components of the system 10. They are also not straight in that the lumens have many curves as they course throughout the body.

As shown in FIG. 5, the guide 18 has a rounded edge surface 92 between the side surface 94 and the front 20. The rounded surface 92 facilitates entry into and positioning within the lumen 90 by providing a contact surface to stretch the lumen especially in those places where the lumen 90 may be constricted or smaller in cross-section than the guide 18 and the graft 12. That is, a corporeal lumen such as a blood vessel or artery can stretch and deform. The rounded surface 92 can urge or force the deformation desired in order to facilitate placement as the guide 18 is urged into and through the lumen 90 by exerting an emplacing force on the exterior end 96 of the rod 24.

The back 22 of the guide 18 has a cavity 98 formed therein. As can be seen, the rod 24 is centrally positioned within the cavity 98 and affixed to the guide 18 to extend rearwardly or downstream 100 through an opening 102 made in the lumen 90 for inserting the pertinent components of the system 10.

As shown in FIG. 5, the proximal end 14 of the graft 12 is positioned within the cavity 98. The graft 12 is preferably sized when in an undeformed condition to be slightly larger in cross-section than the cross-section of the guide 18. The proximal end 14 of graft 12 is collapsed and inserted into the cavity 98. Thereby an external or radial force is exerted outwardly against the interior surface 104 of the cavity 98 to retain the graft 12 and more particularly the proximal end 14 thereof within the cavity 98. Further, the lumen engaging portion of the staples 16 (or FIG. 4) may frictionally engage the interior surface 104 of the guide 18 to further restrain and retain the graft 12 within the cavity 98 during placement in the lumen. The guide 18 is preferably made of a soft material such as Teflon to facilitate the engaging and disengaging of the lumen engaging portion 70, 72 of the staples 16 (or 74 of FIG. 4).

It can be seen from FIG. 5, that an opening 102 is formed in the lumen 90 such as an artery, vessel or other similar corporeal lumen. Appropriately sized system 10 components such as guide 18 and graft 12 (appropriately sized in cross-section and in length 54 and 56) are inserted through the opening 102 and into the lumen 90. The guide 18, with the graft 12 in position as shown in FIG. 5, is urged in. an upstream direction by exerting a positioning force on the exterior end 96 of the rod 24 and exterior end 108 of tube 26 (FIG. 1). Of course, the rod 24 and tube 26 are sized to be of sufficient length 25, 28 so that the guide 18 and graft 12 may be positioned through the lumen 90 to a desired position which may be some distance from the entry point 102. It should be recognized by those skilled in the art that appropriate radiological techniques such as fluoroscopy can be used to assist the user in positioning the guide 18 and in turn the graft 12 at a precise position within the lumen 90. This position, of course, would be a diseased or damaged portion of the lumen 90 which is in need of repair. Upon reaching the desired position within the lumen 90, further forward or upstream movement within the lumen 90 is stopped. The inflation means 36 is then operated to inflate the inflatable membrane 30. The inflatable membrane is desirably partially inflated. Thereupon the exterior end 96 of the rod 24 is again urged into the lumen 90 while the end 97 of the tube 26 is restrained so that the guide 18 disassociates from the graft 12. That is, the inflatable membrane 30 exerts a force outwardly or radially against the interior surface 86 of the graft 12. The exterior end 108 of the tube 26 is then held or restrained by the user while the rod 24 is urged inwardly. The membrane 30 retains the graft 12 in a fixed location as the exterior end 96 of the rod 24 is urged inwardly into the lumen 90 and the guide 18 in turn moves forwardly or upstream within the lumen 90 to disassociate the graft 12 from within the cavity 98 of the guide 18. Thereafter the inflation means 36 is further operated to further inflate the inflatable membrane 30 to in turn apply a radial or outward force 110 against the interior surface 86 of the graft and the legs 62 and 64 of the staples (78, FIG. 4) to cause the lumen engaging portion 70 and 72 of the staples 16 (or 74 of FIG. 4) to engage the lumen.

After the staples are inserted into the lumen 90 by inflating the inflatable membrane, the inflation means 36 is operated to deflate the inflatable membrane 30. After deflation, the tube 26 is withdrawn from within the lumen 90. After removing the tube 26 in its entirety, the rod 24 with the guide means 18 is thereafter removed in its entirety. The back 22 of the guide 18 is formed to have a rounded edge 111 to facilitate removal. Alternately, the tube 26 and guide 18 can be simultaneously withdrawn from the lumen 90. The opening 102 may then be closed.

After emplacement, it can be seen that the pressure of the lumen fluid, for example blood, forces the graft 12 against the lumen interior surface 112 ,to hold the graft 12 in place. The bifolds 50 of the graft 12 permit deformation of the graft 12 to conform to the interior surface 112 of the lumen, Further, the bifolds 50 act somewhat as a mechanical labyrinth seal to reduce leakage between the interior surface of the lumen 112 and the exterior surface 84 of the graft 12. Similarly, the internal pressure of the fluid within the lumen 90 holds the graft 12 in place and prevents leakage at the distal end 88 of the graft 12. That is, again the bifolds 50 of the graft 12 act as a mechanical labyrinth seal to reduce leakage between the interior surface of the lumen 112 and the exterior surface 84 of the graft 12.

In operation, it should be noted that the system 10 with the graft 12 is inserted into the lumen 90 using accepted surgical techniques. For example, an opening could be made through the leg to reach the main artery of a human being. Thereafter, the system 10 could be used as above described to emplace an artificial graft within the main artery as far interior the body as the myocardial or great artery area. This technique therefore avoids major surgery in which the chest or abdomen is penetrated for repair of the aorta, vena cava or the like.

It should further be noted that the staples 16 illustrated in FIG. 3 and in FIG. 4 have axial members 62, 64 and 78 and base members or retention members 60 and 80 to retain them in a proper operable orientation with respect to the graft surface 84. The axial members 62, 64 and 78 also provide a structural member against which the inflatable membrane 30 can interact for receiving the force from the inflatable member 30 as it is inflated to facilitate removal of the graft 12 from the cavity 98 of the guide 18 and to further facilitate the application of force to insert the lumen engaging members 70, 72 and 74 into the lumen 90.

The components of the system 10 are, of course, made of anatomically compatible substances. For example, the guide 18 and rod 24 may be made of a Teflon type material. Further, the tube 26 and inflatable membrane 30 are made of a substantially chemically compatible plastic. Both the rod 24 and tube 26 are made of materials, e.g., Teflon, to be flexible and sized in appropriate diameter and length to facilitate placement of the graft 12 at the desired location within the lumen 90.

It should be noted that the membrane 30 is positioned proximate the cavity end 32 of the tube and sized in length 28, and sufficiently elastic so that the membrane 30, when expanded, contacts the forward portion of the graft 12 and particularly the staples 16, and further applies the force needed to disassociate the graft 12 from the guide 18 and the force necessary to urge the staples 16 into the lumen sidewall.

Use of the system 10 with the graft 12 herein described precludes the need for major surgery to repair a lumen, such as a blood vessel or artery in the great artery area It can also be used to repair other lumens or ductiles within the body of a human being or animal Use of the system thus will reduce the morbidity rates associated with major surgery. It also facilitates rapid repair of defective or damaged lumens at relatively low cost and at low risk The system is mechanically simple and reliable and also useful for treating trauma victims in an emergency context It may be noted that the system 10 herein described, including the graft 12, are purely embodiments of the invention and are merely illustrative of the application of the principles of the invention. Reference herein to details of the illustrated embodiment is not intended to limit the scope of the claims which themselves recite those features regarded as essential to the invention.

I claim:

1. A system for intraluminally engrafting in a fluid conducting corporeal lumen comprising:
a hollow graft of preselected cross-section and length and having a proximal end for placement upstream within said lumen, said graft being deformable to substantially conform to the interior surface of said lumen;
a plurality of staples adapted proximate the proximal end of said graft and extending therethrough for stapling said graft to and within said lumen;
placement means for emplacing said graft into said lumen, for positioning it at a preselected position within said lumen, and for causing at least one of said staples to engage said lumen, said placement means including:
   guide means having a front and back and sized for positioning in said lumen, said guide means having road means adapted to the back thereof sized in length to extend exterior said lumen for manipulation by the user, said guide means back having a cavity formed therein with said rod being centrally positioned within said cavity wherein said proximal end of said graft is retained within said cavity for purposes of positioning said graft in said lumen; and
   operation means for removing said graft from said guide means and for positioning said staples into said lumen; said operation means including a hollow tube for slideable positioning over said rod and sized in length to extend from said cavity to exterior said lumen, said tube having an inflatable membrane proximate the cavity end of said tube, and a channel in communication with said inflatable membrane and extending along the length of said tube, and inflation means connectable to said channel exterior said lumen for inflating and deflating said inflatable membrane.

2. The system of claim 1 wherein said guide means is substantially cylindrical in shape and wherein said guide means front has a rounded edge surface.

3. The system of claim 2 wherein said graft is substantially cylindrical in shape and is larger in cross-section than said guide means, wherein said guide means is made of a material so that said staples at the proximal end of said graft releasably engage the surface of said cavity, and wherein said inflatable membrane when inflated exerts force against said staples so that said guide means is released therefrom upon upstream movement of said guide means and so that said staples are thereupon urged into said lumen.

4. The system of claim 3 wherein each of said staples has a lumen engaging member exterior said graft which member is angulated in a downstream direction and which member has a distal end for engaging said lumen, said lumen engaging member being retained within said cavity with said proximal end of said graft during positioning within said lumen.

5. A method for artificially and intraluminally engrafting in a fluid conducting corporeal lumen comprising:
making an access to and an opening in a corporeal lumen;
providing apparatus for intraluminal engrafting which apparatus includes:
   a hollow graft of preselected cross-section and length and having a proximal end for placement upstream within said lumen, said graft being deformable to substantially conform to the interior surface of said lumen,
   a plurality of staples adapted proximate the proximal end of said graft and extending therethrough for stapling said graft to and within said lumen, guide means having a back with a cavity formed therein and a front, and sized for positioning in said lumen, said guide means having rod means centrally positioned in and secured within said cavity and sized in length to extend exterior said lumen for manipulation, said guide means having means to retain said proximal end of said graft for positioning of said graft in said lumen, a hollow tube for slideable positioning over said rod and sized in length to extend from said cavity to exterior said lumen, said tube having an inflatable membrane proximate the cavity end of said tube, and a channel in communication with said tube and inflation means connectable to said channel exterior said lumen for inflating and deflating said inflatable membrane;

inserting said guide means and hollow graft into said opening and urging said guide means and hollow graft upstream in said lumen to a desired location therewithin;

operating said inflation means and said guide means to disassociate said graft from said guide means and to cause at least one staple to engage the lumen;

operating said inflation means and said guide means to remove them from said lumen; and closing said opening and said access.

6. The method of claim 5 wherein fluoroscopy means are provided and monitored to ascertain the movement and positioning of said guide means and graft.

7. The method of claim 5 wherein said inflation means is operated to cause the inflatable membrane to apply force to the staples to urge the staples into the lumen.

* * * * *